(12) United States Patent
Kobayashi et al.

(10) Patent No.: US 9,395,282 B2
(45) Date of Patent: Jul. 19, 2016

(54) ISOLATOR SYSTEM

(71) Applicant: PANASONIC HEALTHCARE HOLDINGS CO., LTD., Tokyo (JP)

(72) Inventors: Koichi Kobayashi, Tochigi (JP); Yasuhiko Yokoi, Hyogo (JP)

(73) Assignee: PANASONIC HEALTHCARE HOLDINGS CO., LTD., Tokyo (JP)

( * ) Notice: Subject to any disclaimer, the term of this patent is extended or adjusted under 35 U.S.C. 154(b) by 0 days.

(21) Appl. No.: 14/645,126

(22) Filed: Mar. 11, 2015

(65) Prior Publication Data

US 2015/0185121 A1  Jul. 2, 2015

Related U.S. Application Data

(63) Continuation of application No. PCT/JP2014/001724, filed on Mar. 25, 2014.

(30) Foreign Application Priority Data

Mar. 29, 2013 (JP) .................................. 2013-071693

(51) Int. Cl.
*B01L 99/00* (2010.01)
*G01N 1/28* (2006.01)
(Continued)

(52) U.S. Cl.
CPC ... *G01N 1/28* (2013.01); *A61L 2/00* (2013.01); *A61L 2/22* (2013.01); *A61L 9/00* (2013.01); *A61L 9/14* (2013.01); *B01L 1/02* (2013.01); *B01L 1/04* (2013.01); *C12M 37/00* (2013.01); *A61L 2202/23* (2013.01); *A61L 2209/14* (2013.01); *B01L 2200/028* (2013.01)

(58) Field of Classification Search
CPC ............. B01L 1/00; B01L 1/02; B01L 1/025; B01L 1/04
USPC .......................................................... 422/567
See application file for complete search history.

(56) References Cited

U.S. PATENT DOCUMENTS 4,022,579 A * 5/1977 Revillet et al. .................. 422/65
4,262,091 A   4/1981 Cox
(Continued)

FOREIGN PATENT DOCUMENTS

JP    10-507075 A    7/1998
JP    2001-507240 A  6/2001
(Continued)

OTHER PUBLICATIONS

International Search Report issued in PCT/JP2014/001724, dated Jun. 17, 2014, with English translation.

*Primary Examiner* — Jill Warden
*Assistant Examiner* — Dwayne K Handy
(74) *Attorney, Agent, or Firm* — McDermott Will & Emery LLP

(57) ABSTRACT

An isolator system includes first and second isolators respectively forming first and second workspaces hermetically sealed from ambient environment, and a pass box provided between the first and second isolators and forming a transport space enabled to communicate the first and second workspaces while maintaining hermeticity, wherein the pass box has a tray on which an article used in work is mounted, and a moving mechanism enabling movement of the tray toward directions to both sides of the first and second isolators, the tray has a first end on the first isolator side located in the first workspace when moved to the first isolator side, and a second end on the second isolator side located in the second workspace when moved to the second isolator side, and the first and second ends of the tray each has a grip bended downward from a mounting face of the tray.

11 Claims, 11 Drawing Sheets

(51) Int. Cl.
  *C12M 1/12* (2006.01)
  *B01L 1/02* (2006.01)
  *B01L 1/04* (2006.01)
  *A61L 2/00* (2006.01)
  *A61L 9/00* (2006.01)
  *A61L 2/22* (2006.01)
  *A61L 9/14* (2006.01)

(56) References Cited

U.S. PATENT DOCUMENTS

| | | | |
|---|---|---|---|
| 4,892,830 A * | 1/1990 | Findley et al. | 435/286.6 |
| 5,861,305 A | 1/1999 | Silley et al. | |
| 6,465,244 B1 | 10/2002 | Annable et al. | |
| 2007/0202797 A1 | 8/2007 | Ishibashi | |
| 2011/0027146 A1 | 2/2011 | Yokoi et al. | |

FOREIGN PATENT DOCUMENTS

| | | |
|---|---|---|
| JP | 2001-308551 A | 11/2001 |
| JP | 2005-102570 A | 4/2005 |
| JP | 2008-134049 A | 6/2008 |
| JP | 2009-222343 A | 10/2009 |
| JP | 2011-030655 A | 2/2011 |
| JP | 2011-177091 A | 9/2011 |
| JP | 2013-204910 A | 10/2013 |

* cited by examiner

ISOLATOR SYSTEM

CROSS-REFERENCE TO RELATED APPLICATIONS

This is a continuation application of International Patent Application No. PCT/JP2014/001724 filed Mar. 25, 2014, which claims the benefit of priority to Japanese Patent Application No. 2013-71693 filed Mar. 29, 2013. The full contents of the International Patent Application are incorporated herein by reference.

BACKGROUND

1. Technical Field

The present disclosure relates to an isolator system used for devices in testing environments related to regenerative medicine and pharmaceutical production.

2. Description of the Related Art

Japanese Patent Application Laid-Open Publication No. 2011-177091 discloses an isolator system used in cell manipulation, culture works and the like. This isolator system includes an isolator that forms a workspace hermetically sealed from the ambient environment and a pass box connected to the isolator. Hereby, articles used for the works can be introduced into the workspace isolated from the outside through the pass box which can be accessed from the outside.

Thus, the present disclosure provides an isolator system that has improved transportation workability of articles used for works in a case where a plurality of isolators is in a connected state.

SUMMARY

An isolator system according to an aspect of the present disclosure, includes a first isolator forming a first workspace being hermetically sealed from an ambient environment, a second isolator forming a second workspace being hermetically sealed from the ambient environment, and a pass box provided between the first isolator and the second isolator and forming a transport space enabled to communicate the first workspace and the second workspace while maintaining hermeticity, wherein the pass box has a tray on which an article used in work is mounted, and a moving mechanism configured to enable movement of the tray toward directions to both sides of the first isolator and the second isolator, the tray has a first end on the first isolator side located in the first workspace when moved to the first isolator side, and a second end on the second isolator side located in the second workspace when moved to the second isolator side, and the first end and the second end of the tray each has a grip bended downward from a mounting face of the tray.

Other features of the present disclosure will become apparent from descriptions of this specification and of the accompanying drawings.

BRIEF DESCRIPTION OF THE DRAWINGS

For more thorough understanding of the present disclosure and advantages thereof, the following description should be read in conjunction with the accompanying drawings, in which.

DETAILED DESCRIPTION

At least the following details will become apparent from descriptions of this specification and of the accompanying drawings.

A detailed description of the embodiments will be given in the following with reference to the drawings, appropriately. However, there may be a case where a detailed description beyond necessity is omitted. For example, there may be a case where a detailed description on a matter already well known or a duplicate description on a configuration substantially the same is omitted. This is for the purpose of avoiding the following description from becoming unnecessarily redundant and facilitating the understandings of those skilled in the art.

Note that the inventors provide the accompanying drawings and the following description for allowing those skilled in the art to fully understand the present disclosure and is not intended to limit the subject described in the scope of claim for patent.

First Embodiment

Description of the isolator system 100 in embodiment 1 will be given in the following with reference to FIGS. 1 to 9, as an example of the isolator system.

The isolator system 100 according to embodiment 1 is an apparatus for performing works of, for example, culturing, manipulation, observation and the like of cells in a sterilized environment. Note that, sterilization means killing microorganisms, cells and the like establishing the highest degree of aseptic condition possible.

In the present embodiment, the Z axis is the axis which is oriented along the vertical direction in which the isolator system 100 is installed in a standing manner, and the direction toward the upper side is set as the +Z direction and the direction toward the downside (underside) is set as the −Z direction. The Y axis is an axis oriented along the direction intersecting the front face and the back face of the isolator system 100, and a direction from the front face where an opening for performing works in the interior of the workspace is provided toward the back face which is on the opposite side of the front face is set as the −Y direction, and the direction from the back face toward the front face is set as the +Y direction. The X axis is an axis oriented along a direction intersecting the right and left side faces seen from the front face and a direction from the left side face, seen from the front, toward the right side face is set as the +X direction and a direction from the right side face to the left side face is set as the −X direction.

[1-1. Overall Structure]

Figure 1:
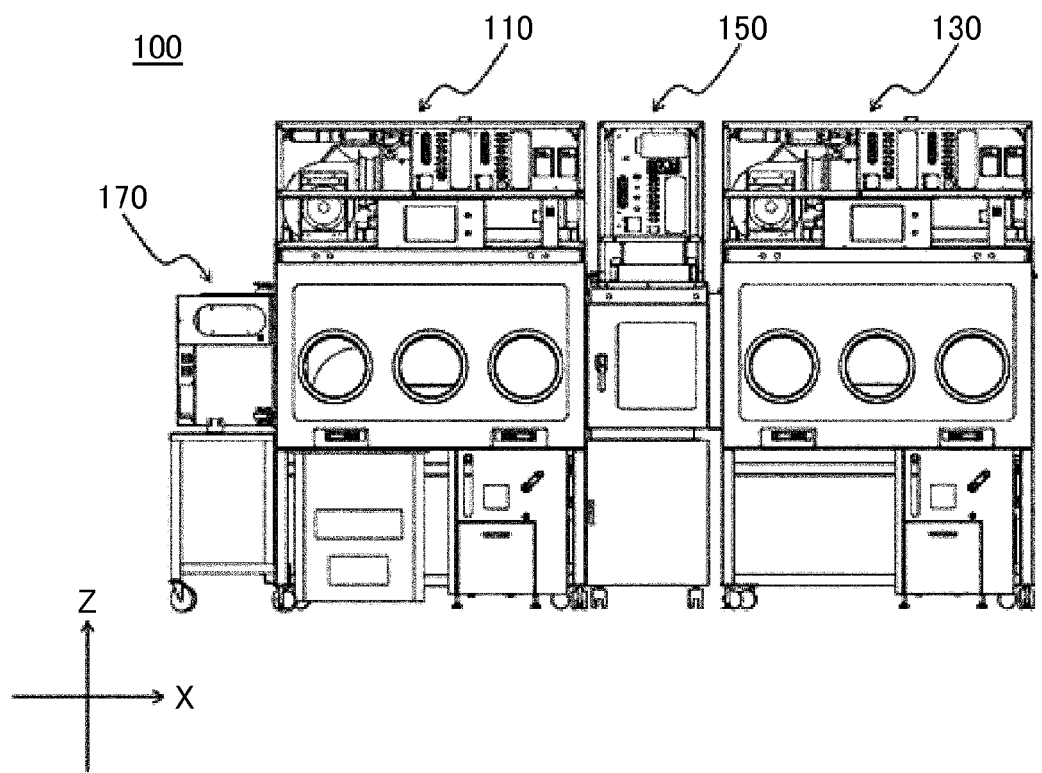
FIG. 1 is an exemplary front view of an isolator system according to a first embodiment.
Figure 2:
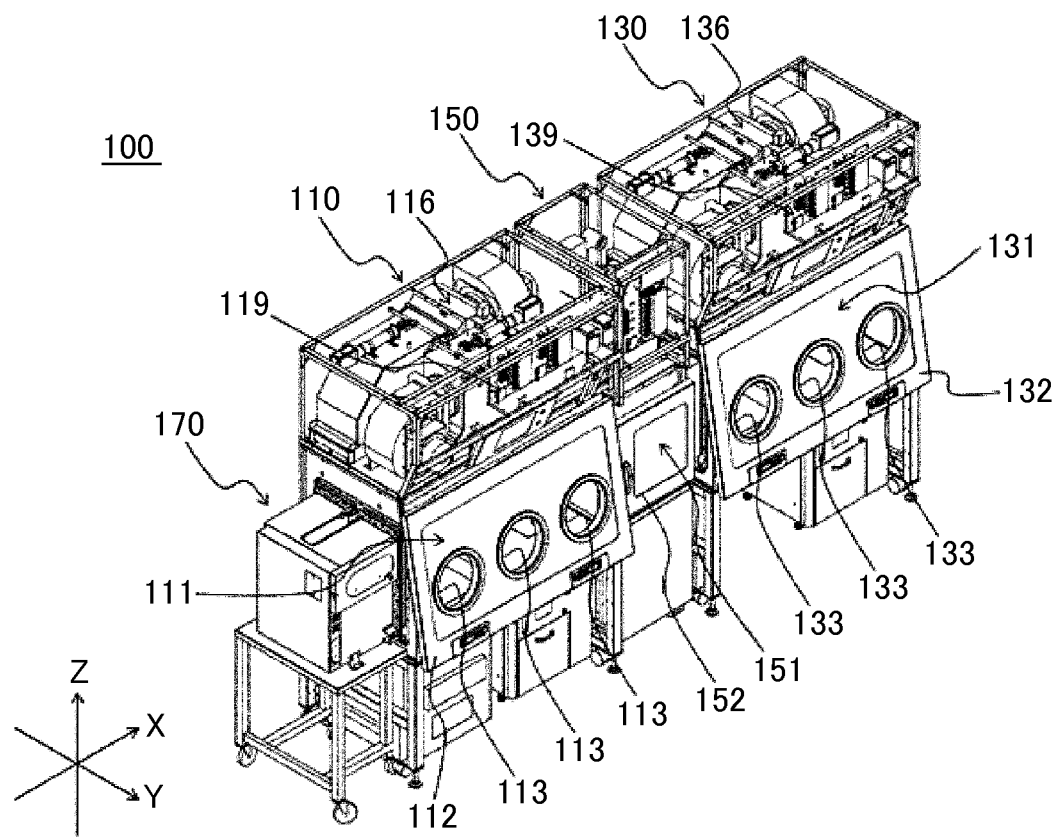
FIG. 2 is an exemplary perspective view of the isolator system according to the first embodiment.
Figure 3:
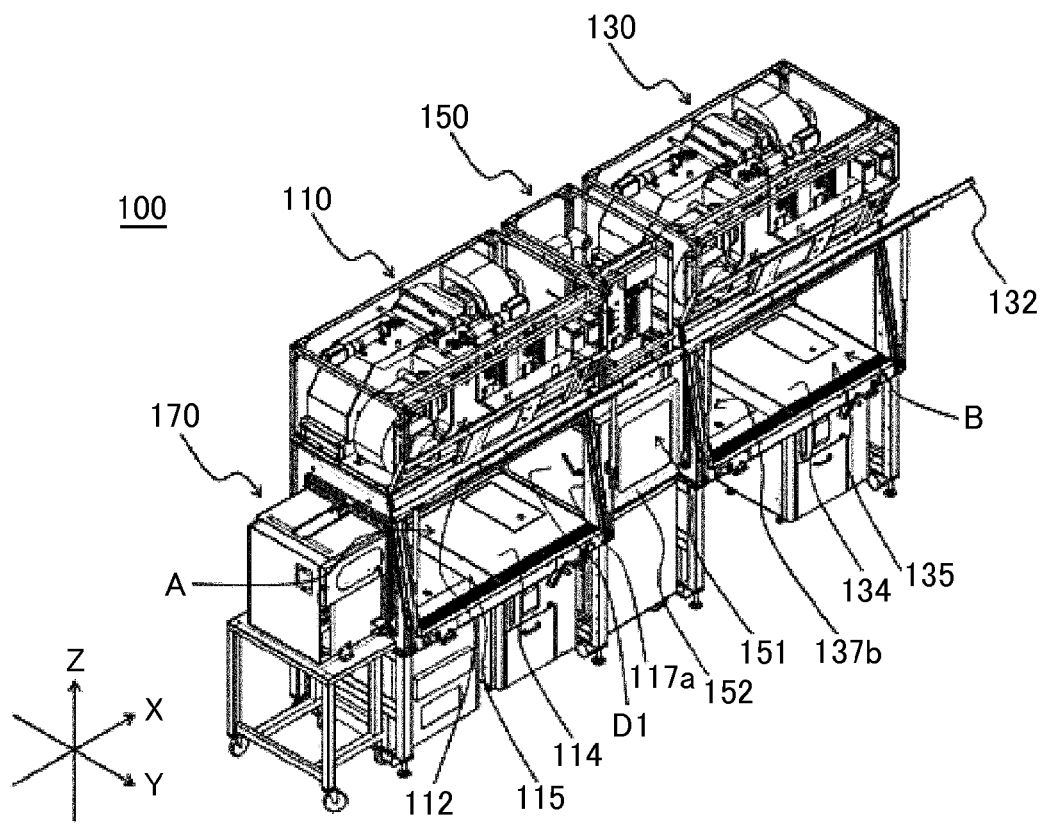
FIG. 3 is an exemplary perspective view of the isolator system according to the first embodiment.

FIG. 1 is a front view of the isolator system 100 according to embodiment 1. FIGS. 2 and 3 are perspective views of the isolator system 100 according to the embodiment 1, showing the opened and closed states.

The isolator system 100 according to embodiment 1, as shown in FIG. 1, includes a first isolator 110, a second isolator 130, a pass box 150 and an incubator 170, and each of the devices are connected in a hermetical manner.

[1-2. Structure of the First Isolator]

The first isolator 110 has a first main body case 111, an air conditioning unit 116 and a control unit 119, as illustrated in FIG. 2.

The first main body case 111 is structured with a front face plate 112, a bottom plate 114 being the work platform 114, a back plate, a top plate, and right and left side face plates 117a, 117b, to form a box-like first work space A. The first main body case 111 is sectioned as the first work space A which has intrusion of bacteria from outside restrained with, for example, a rectangular parallelepiped box body. The first isolator 110 is structured with a bottom plate 114, a back face plate, a top plate, and right and left side plates 117a, 117b made of stainless steel plates which allows easy cleaning and sterilization.

The front face plate 112 is configured of a glass plate and has provided to the front face a plurality of openings 113 which are the parts for the worker's hands to be inserted. The plurality of the openings 113 each has a glove (not shown) attached. The front faceplate 112 can be opened and closed with the hinge provided at the upper end as the axis. Hereby, the front face opening of the first main body case 111 can be opened and closed. The right and left side face plates 117a, 117b have provided thereto openings for mounting the pass box 150 and the incubator 170. The first isolator 110 has the pass box 150 mounted to the right opening H1 (first opening) on the right side face plate 117a, and the first door D1 of the first hatch 153 of the pass box 150 configures a part of the right side face plate 117a. Further, the left opening (not shown) of the left side face plate 117b has an incubator 170 mounted thereto and the door (not shown) of the incubator 170 configures a part of the left side face plate 117b. A worker performs work in the first main body case 111 through the glove during work. The top plate has provided a hanging bar (not shown) for hanging matters used in the works.

The air conditioning unit 116 is provided above the first main body case 111 for air conditioning in the first work space A. The air conditioning unit 116 has a gas feeding inlet (not shown) provided to the top plate inside the first main body case 111 and a gas discharge outlet (not shown) provided to the front face side and the back face side of the bottom plate 114. The first main body case 111 has air fed from the gas feeding inlet and air discharged from the gas discharge outlet. In an isolator in general, a particulate trap filter such as a HEPA filter is provided to the gas feeding inlet for securing a sterile environment inside the main body case, and air is fed into the main body case through the particulate trap filter. Further, the gas discharge outlet also has a particulate trap filter provided thereto and the air inside the workspace is discharged from the main body case through the particulate trap filter. Additionally, an isolator has sterilized material such as oxygenated water sprayed inside the main body case and sterilization is performed for sterilizing inside the main body case.

The control unit 119 is provided above the first main body case 111 and controls the air conditioning unit 116, the temperature control unit and the like.

Further, the first isolator 110 in addition has under the first main body case 111 experimental devices required for performing experiments such as an observation device and a centrifuge, and a sterilized gas generating device. The experimental devices are provided accessible from the first workspace A.

[1-3. Second Isolator Structure]

As illustrated in FIGS. 2 and 3, the structure of the second isolator 130 differs from the structure of the first isolator 110 to some degree due to the differences in the various devices mounted and their positions, however, the basic structure is the same.

The second isolator 130 has a main body case 131, an air conditioning unit 136 and a control unit 139, as illustrated in FIG. 2.

The second main body case 131 is structured with a front face plate 132, a bottom plate 134 being the work platform 134, a back plate, a top plate, and right and left side face plates 137a, 137b, to form a box-like second work space B. The second main body case 131 is sectioned as the second work space B which has intrusion of bacteria from outside restrained with, for example, a rectangular parallelepiped box body. The second isolator 130 is structured with a bottom plate 134, a back face plate, a top plate, and right and left side plates 137a, 137b made of stainless steel plates which allows easy cleaning and sterilization.

The front face plate 132 is configured of a glass plate and has provided to the front face a plurality of openings 133 which are the parts for the worker's hands to be inserted. The plurality of the openings 133 each has a glove (not shown) attached. The right and left side face plates 137a, 137b have provided thereto openings for mounting the pass box 150 and the incubator. The second isolator 130 has the pass box 150 mounted to the second opening H2 (second opening) on the left side face plate 137b, and the second door D2 of the second hatch 154 of the pass box 150 configures a part of the left side face plate 137b. Further, although an opening is not provided to the right side face plate 137a in the second isolator 130, an opening may be provided to mount the second incubator 170. In this case, the door (not shown) of the incubator 170 configures a part of the right side face plate 137a. A worker performs work in the second main body case 131 through the glove during work. The top plate has provided a hanging bar (not shown) for hanging matters used in the works.

The air conditioning unit 136 is provided above the second main body case 131 for air conditioning in the second work space B. The air conditioning unit 136 has a gas feeding inlet (not shown) provided to the top plate inside the second main body case 131 and a gas discharge outlet (not shown) provided to the front face side and the back face side of the bottom plate 134. The second main body case 131 has air fed from the gas feeding inlet and air discharged from the gas discharge outlet.

The control unit 139 is provided above the second main body case 131 and controls the air conditioning unit 136, the temperature control unit and the like.

Further, the second isolator 130 in addition has under the second main body case 131 experimental devices required for performing experiments such as an observation device and a centrifuge, and a sterilized gas generating device. The experimental devices are provided accessible from the second workspace B. The isolator system 100 according to the embodiment 1 has each of the first and the second isolators 110, 130 include a control unit, an air conditioning unit and various devices, however, a structure that has the isolators share a single one of the devices may be adopted. Hereby, the space can be saved and the cost reduced.

[1-4. Structure of the Pass Box]

The pass box 150 is provided for a worker to insert work material inside the first isolator 110 and the second isolator 130 from outside. Further, the pass box 150 is provided to allow the worker to move work material between the first isolator 110 and the second isolator 130. The pass box 150 includes a box-like delivery case 151 that forms a transport space C that temporarily stores work material. A front opening 158 is provided on the front face of the delivery case 151 and the front opening 158 has provided thereto a front door 152 that separates the transport space C that is hermetically sealed from the ambient environment and the exterior. Further, the left and right side faces of the delivery case 151 have first and second delivery openings 153, 154 provided. The first delivery opening 153 is mounted to the first opening H1 of the right side face plate 117a of the first isolator 110, and communicates the transport space C of the pass box 150 and the first workspace A of the first isolator 110. Similarly, the second delivery opening 154 is mounted to the second opening H2 of the left side face plate 137b of the second isolator 130, and communicates the transport space C of the pass box 150 and the second workspace B of the second isolator 130. The first and second delivery openings 153, 154 respectively have attached first and second doors D1, D2 which can open and close. The first door D1 of the first delivery opening 153 separates the transport space C inside the delivery case 151 and the first workspace A inside the first main body case 111, and the second door D2 of the second delivery opening 154 separates the transport space C inside the delivery case 151 and the second workspace B inside the second main body case 131.

Figure 4:
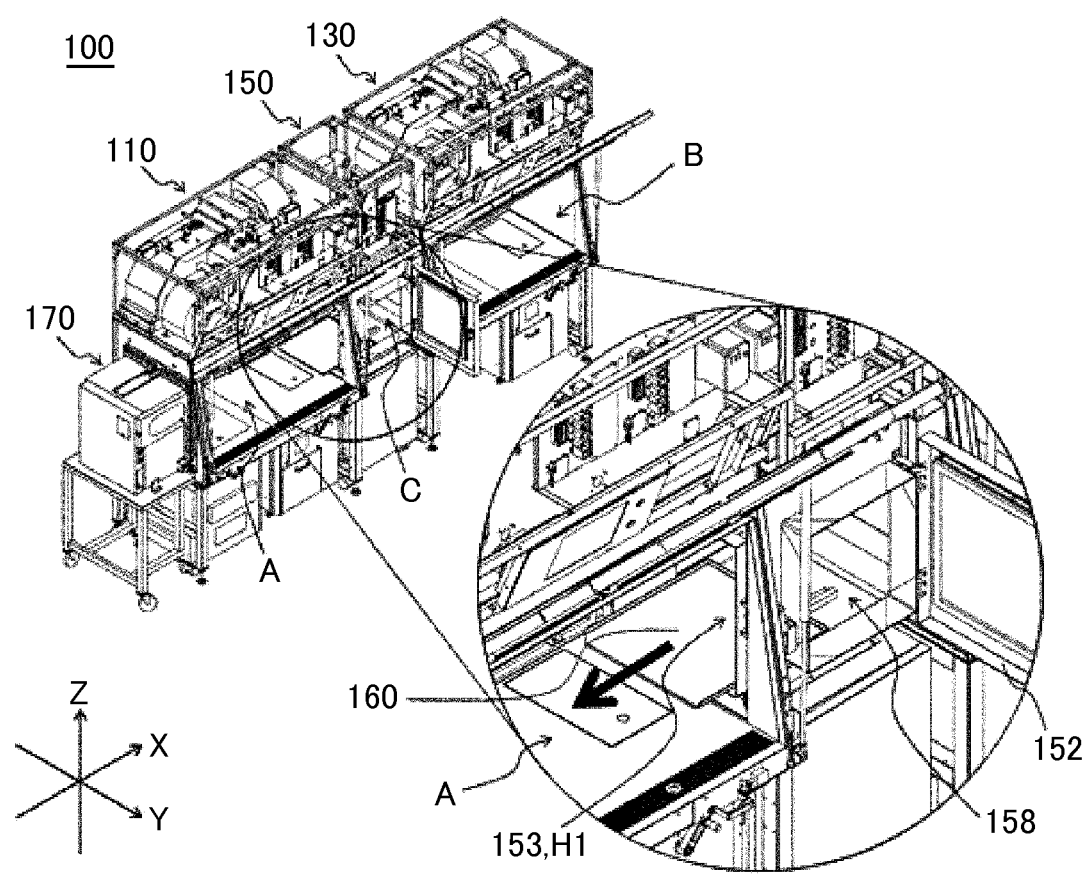
FIG. 4 is an exemplary perspective view of the isolator system and an enlarged perspective view of the periphery of the tray according to the first embodiment.
Figure 5:
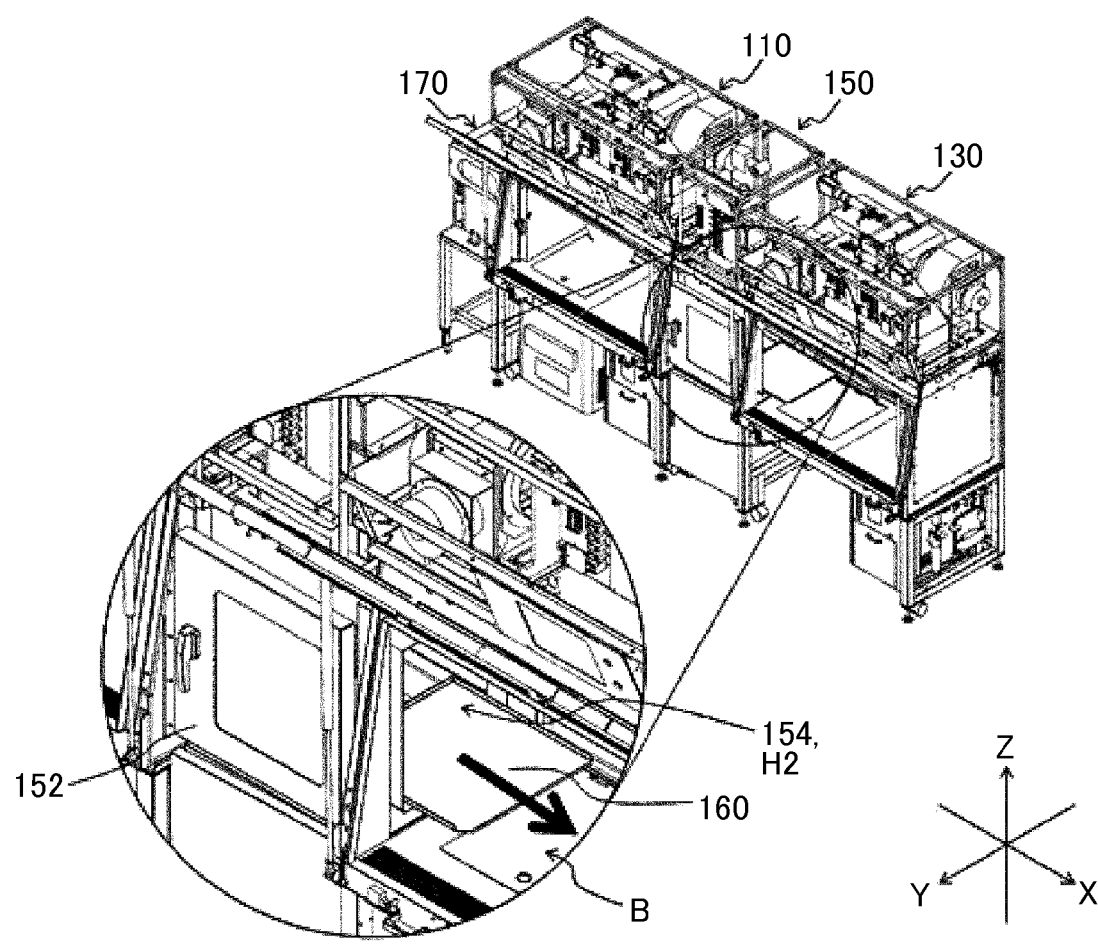
FIG. 5 is an exemplary perspective view of the isolator system and an enlarged perspective view of the periphery of the tray according to the first embodiment.

FIGS. 4 and 5 illustrate perspective views of the isolator system 100 according to the first embodiment 1 and enlarged views of the periphery of the tray 160.

The delivery case 151 forms the inner transport space C with the bottom plate 155, the top plate, the back face plate, right and left side face plates and the front face door 152. The bottom plate 155 has provided thereto a tray 160 for placing articles used for work and the tray 160 is movable to the right and left with the later described moving mechanism.

[1-5. Structure of Incubator]

The incubator 170 includes a storage chamber (not shown) inside. This storage chamber is a room for accommodating culture and is partitioned as a space having intrusion of bacteria from outside restrained with, for example, a rectangular parallelepiped body. The storage chamber according to the present embodiment is partitioned with a stainless steel plate. The incubator 170 is structured detachable from the first isolator 110. Hereby, culture can be managed in units of the incubators 170. For example, problems of such as misidentification and the like of cultures can be restrained by using incubators 170 that are dedicated to each donor.

[1-6. Structure of Moving Mechanism]

Description of the moving mechanism of the tray will be given with reference to FIGS. 6 to 11.

Figure 6:
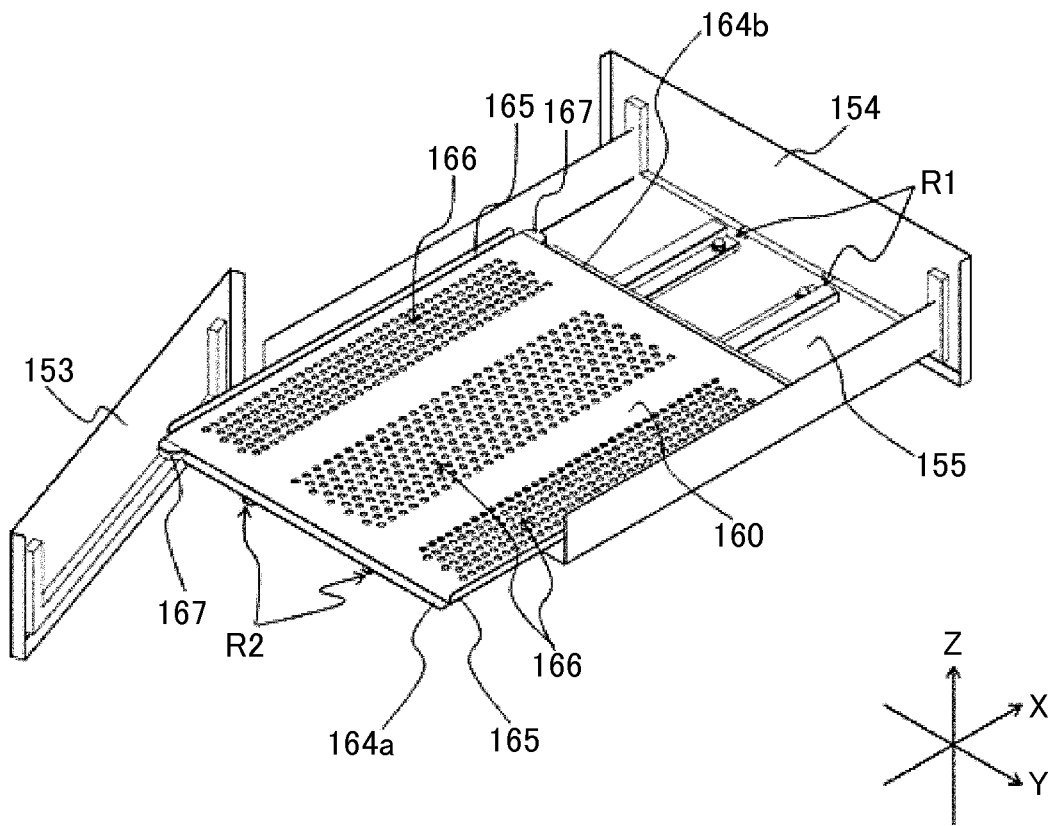
FIG. 6 is an exemplary perspective view illustrating a configuration of the periphery of the slide tray according to the first embodiment.
Figure 7:
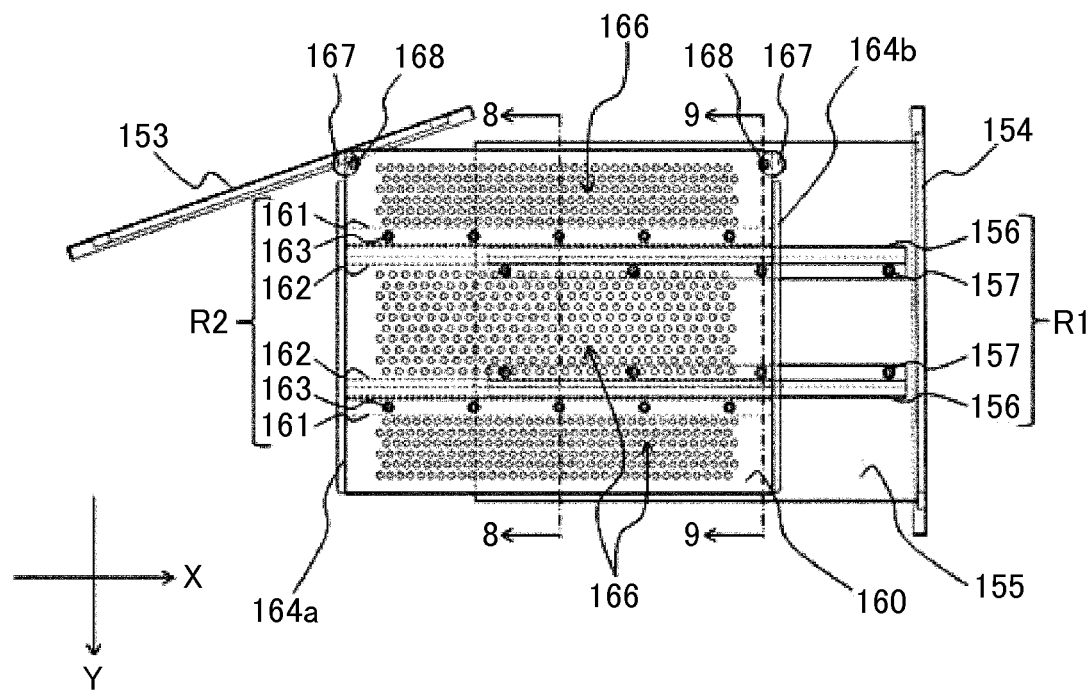
FIG. 7 is an exemplary top view illustrating the configuration of the periphery of the slide tray according to the first embodiment.
Figure 8:
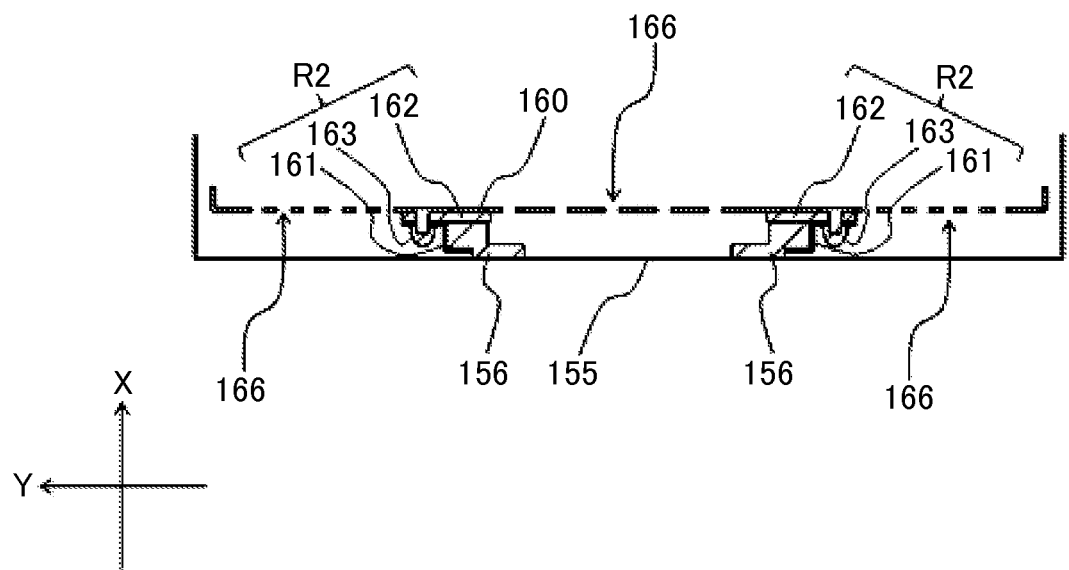
FIG. 8 is an exemplary end face view along line 8-8 of FIG. 7.
Figure 9:
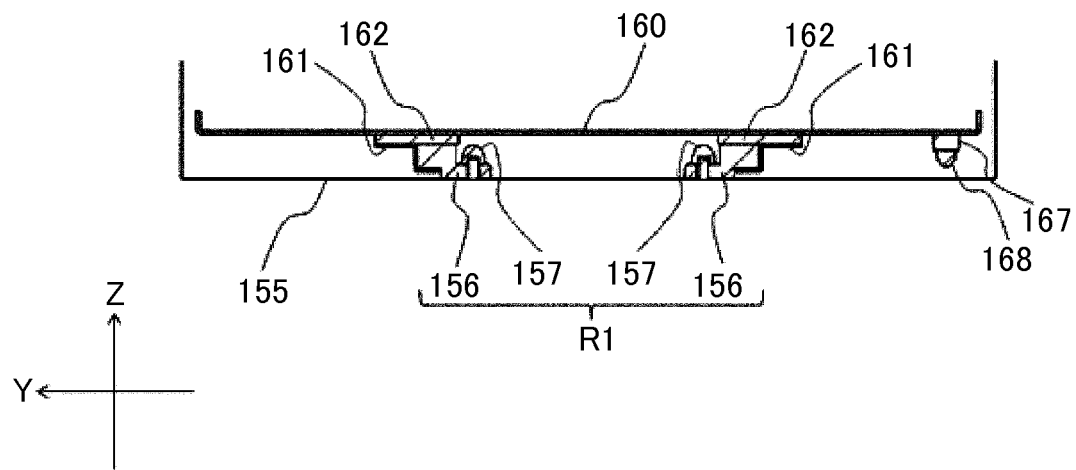
FIG. 9 is an exemplary end face view along line 9-9 of FIG. 7.

FIG. 6 is a perspective view illustrating the configuration of the periphery of the slide tray according to embodiment 1, and FIG. 7 is a top view thereof. FIG. 8 is an end face view along line 8-8 of FIG. 7 and FIG. 9 is an end face view along line 9-9 of FIG. 7.

As illustrated in FIGS. 6 and 7, the tray 160 is movably attached on the bottom plate 155 of the transport space C. The bottom plate 155 has rails R1 (first engaging part) mounted. The rails R1 are engaged with the rails R2 (second engaging part) mounted to the back face of the mounting face of the tray 160. The rails R1 and R2 configure the moving mechanism that enables the tray 160 to move. The tray 160 has a plurality of penetrating holes 166 that are formed to penetrate from the mounting face to the back face so to enable sterilized gas to come around easily. Both ends of the tray 160 in the moving direction (X direction) have grips 164a, 164b formed in a manner curved downward from the mounting face. Therefore, the tray 160 can be easily pulled out into the first workspace A or the second workspace B by the worker holding and pulling the grips 164a, 164b when moving the tray 160. Additionally, the two ends in the direction (Y direction) orthogonal to the moving direction of the tray 160 have erected parts 165 formed to erect upward from the mounting face. Thereby, articles used for work are restrained from dropping when the tray 160 is moved to the first workspace A or the second workspace B while in a state having the articles placed on the mounting face. Further, a cushion member 167 is attached with a nut 168 to the corner of the tray 160 on the rotating axis side (−Y direction side) of the first and the second doors D1, D2. The cushion member 167 is a resin or a silicon member having a curved surface and is provided to abut against the first and the second doors D1, D2 with the curved surface. Therefore, the cushion member 167 not only restrains the first and the second doors D1, D2 and the tray 160 from being damaged when the tray 160 comes into contact with the first and the second doors D1, D2, but also restrains dust (particles) from being generated by a hitting. Furthermore, a stopper for restraining the moving range of the tray 160 is provided to the moving mechanism. Note that, the description of the stopper will be given later. The stopper restrains a worker from excessively pulling the tray 160 thereby enabling to restrain articles from dropping and the like.

Figure 10:
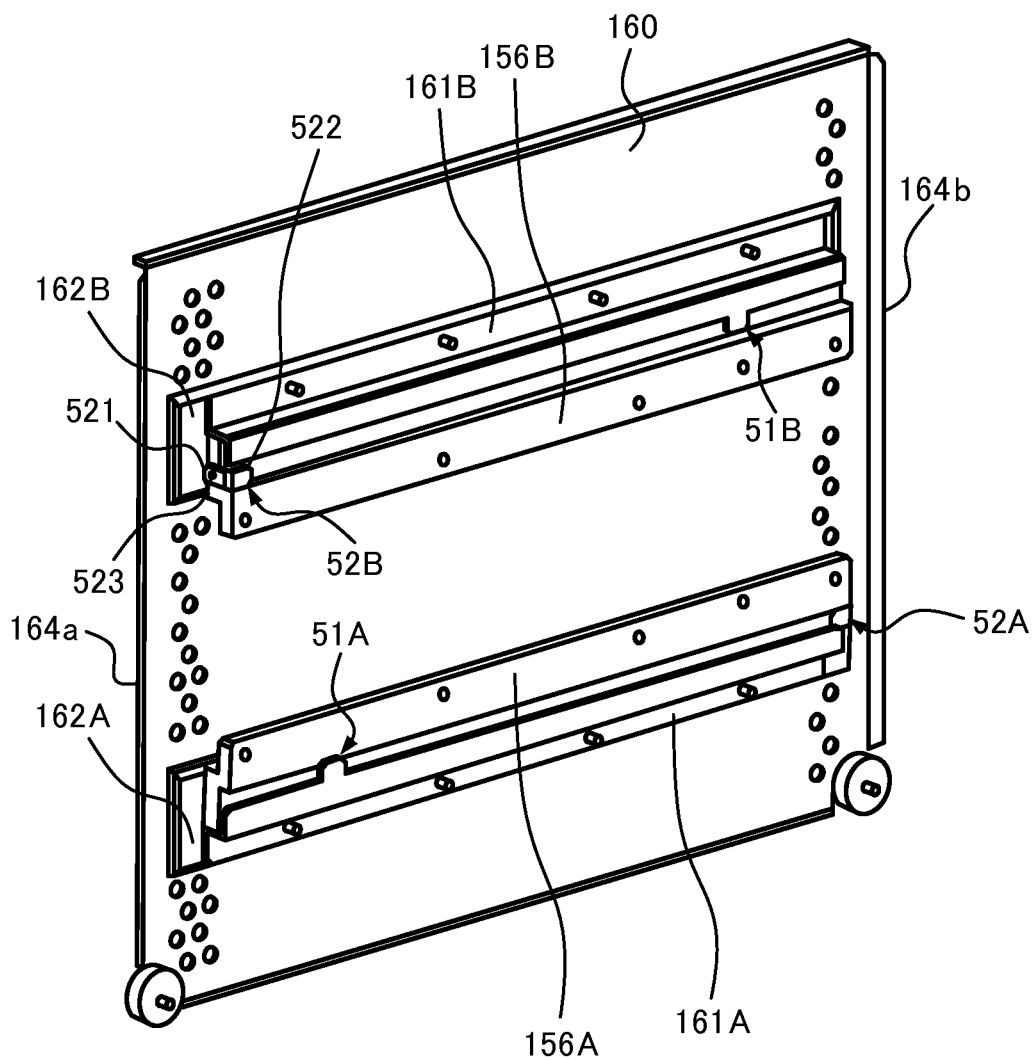
FIG. 10 is an exemplary perspective view illustrating a first and a second rail according to the first embodiment.
Figure 11:
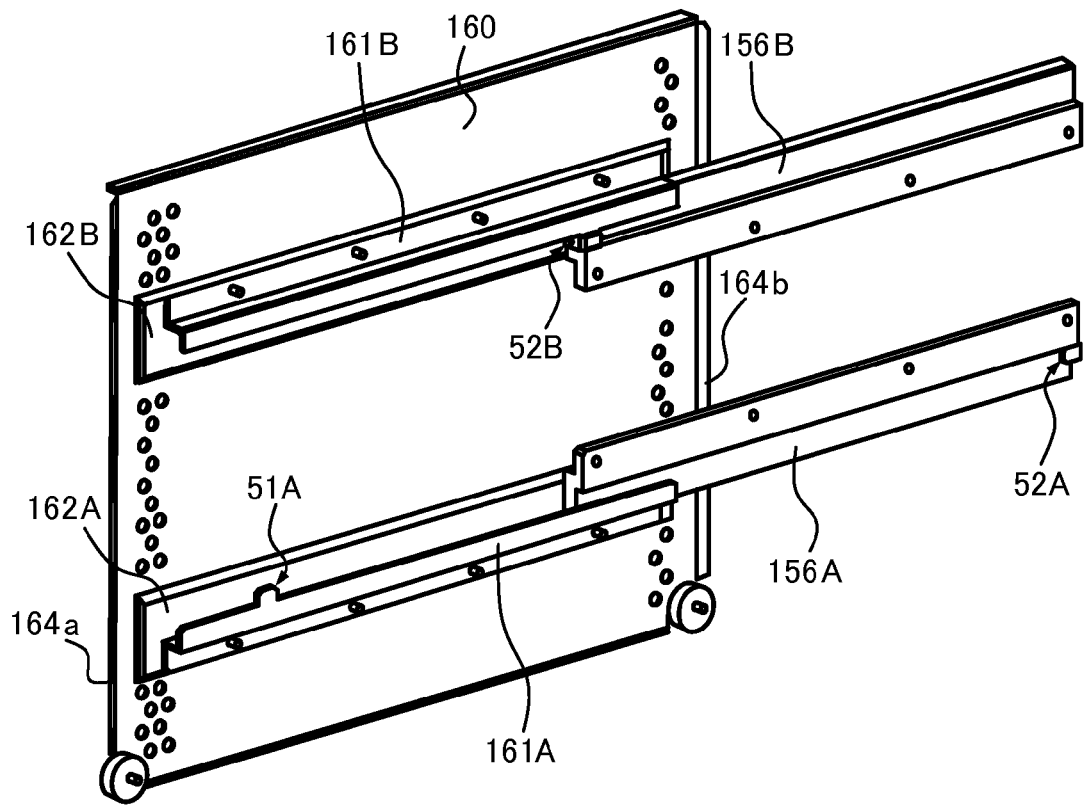
FIG. 11 is an exemplary perspective view illustrating the first and the second rail according to the first embodiment.
Figure 11:
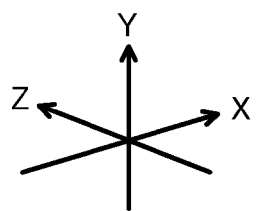

Description of the rails R1 and R2 that configure the moving mechanism of the tray 160 will be given next with reference to FIGS. 8 to 11. FIGS. 10 and 11 are perspective views illustrating the first and second rails according to embodiment 1. FIGS. 10 and 11 illustrate the tray 160 etc. seen from below (−Z) toward above (+Z). FIG. 10 illustrates the tray 160 in a state when provided inside the pas box 150 (FIG. 5). FIG. 11 illustrates the tray 160 in a state when moved to the first workspace A side. Note that, the first guide units 156A, 156B in FIGS. 10 and 11 respectively correspond to the first guide unit 156 on the −Y side and the first guide unit 156 on the +Y side of the two first guide units 156 in FIG. 9. Further, the second guide units 161A, 161B in FIGS. 10 and 11 respectively correspond to the second guide unit 161 on the −Y side and the second guide unit 161 on the +Y side of the two second guide units 161 in FIG. 9. Furthermore, the spacers 162A, 162B in FIGS. 10 and 11 respectively correspond to the spacer 162 on the −Y side and the spacer 162 on the +Y side of the two spacers 162 in FIG. 9. Note that in FIGS. 10 and 11, descriptions of the plurality of holes are partially omitted.

The rails R1 and R2 are used for moving the tray 160 along the X direction between the first location and the second location. The first location is a location in the first workspace A. When the tray 160 is moved to the first location, at least the grip 164a of the grips 164a and 164b will be provided in the first workspace A. The second location is a location at, for example, the opposite side of the first location in the X direction with regard to the transport space C. The second location is a location in the second workspace B. When the tray 160 is moved to the second location, at least the grip 164*b* of the grips 164*a* and 164*b* will be provided in the second workspace B.

The rail R1 (FIG. 9) includes the first guide units 156 and nuts 157 which fix the first guide units 156 to the bottom plate 155. The first guide units 156 are formed with resin. The first guide units 156 are in elongated shapes extending along the X direction. The two first guide units 156 are provided in parallel to the X direction. The two first guide units 156 (156A, B in FIGS. 10 and 11) are arranged in the Y direction intersecting the moving direction (X direction). The two first guide units 156 are each configured of a part (also called the "first part") fixed to the bottom plate 155 with the nuts 157, a part (also called the "second part") extending to erect upward (+Z direction) from the part which is to be fixed, and a part (also called the "third part") bending in the outward direction (Y direction) between the two first guide units 156 above the part extending upward. Hereby, a space (gap) for the second guide unit 161 to enter is formed between the bended part of the first guide unit 156 and the bottom plate 155. In other words, the one first guide unit 156A (second rail) of the two first guide units 156 has the aforementioned first to third parts, and is bended such that a space (also called a "first space") is formed between the third part of the first guide unit 156A and the bottom plate 155. The third part of the first guide unit 156A is bended in the Y direction toward the direction (−Y) apart from the other first guide unit 156B. Further, the first guide unit 156B (first rail) has the aforementioned first to third parts, and is bended to form a space (also called a "second space") between the third part (second bended piece) of the first guide unit 156B and the bottom plate 155. The third part (first bended piece) of the first guide unit 156B is bended in the Y direction toward the direction (+Y) apart from the first guide unit 156A.

The rail R2 includes second guide units 161 and spacers 162 positioned between the tray 160 and the second guide units 161, and nuts 163 for fixing the second guide units 161 and the spacers to the back face of the tray 160. The second guide units 161 are formed with stainless steel plates which are made of metal. The spacers 162 are formed of resin. The second guide units 161 are in elongated shapes extending along the X direction. The two second guide units 161 are provided in parallel (X direction) to the first guide unit 156. The two second guide units 161 (161A, B in FIGS. 10 and 11) are arranged in the Y direction intersecting the moving direction (X direction). The two second guide units 161 are each configured of a part (also called the "fourth part") fixed to the spacer 162 (162A, B in FIGS. 10, 11) with the nuts 163, a part (also called the "fifth part") extending to bend downward (−Z direction) from the part which is to be fixed to the spacer 162, and a part (also called the "sixth part") bending in the inward direction (Y direction) between the two second guide units 161 below the part extending downward. Hereby, a space for the first guide unit 156 to enter is formed between the second guide unit 161 and the spacer 162. In other words, the second guide unit 161A (fourth rail) has the aforementioned fourth to sixth parts and the sixth part (second inserting piece) of the second guide unit 161A is bended to be inserted in the first space. The sixth part of the second guide unit 161A is bended in the Y direction toward the direction (+Y) approaching the second guide unit 161B. And the second guide unit 161B (third rail) has the aforementioned fourth to sixth parts and the sixth part (first inserting piece) of the second guide unit 161B is bended to be inserted in the second space. The sixth part of the second guide unit 161B is bended in the Y direction toward the direction (−Y) approaching the second guide unit 161A. Here the spacers 162 are provided so that the grips 164*a*, 164*b* formed to the two ends of the tray 160 in the moving direction (X direction) do not hit the first guide unit 156 when the tray 160 is moved.

With the above configuration, the rails R1 and R2 are engaged so that the first guide unit 156 and the second guide unit 161 engage in a latching manner while the tray 160 is freely movable in both sides in the X direction. The rails R1 and R2 are engaged in a manner prevented from moving away from each other in the Z direction by the first guide unit 156 and the second guide unit 161 being engaged.

Description of the first and the second stoppers that restrain the movement of the tray 160 will be given in the following with reference to FIGS. 10 and 11.

<Structure>

The first guide unit 156B and the second guide unit 161B have provided a protrusion 51B (first protruding piece) and a rest 52B (first abutment) that exhibit a function as the first stopper. The protrusion 51B and the rest 52B restrain the tray 160 moved to the first location from moving further to the first isolator 110 side (−X).

The protrusion 51B is a protruding piece that protrudes from the sixth part of the second guide unit 161B toward the −Y side in the second space. For example, the protrusion 51B is provided on the +X side with regard to approximately the center of the second guide unit 161B in the longitudinal direction (X direction) of the second guide unit 161B.

The rest 52B is an abutment that abuts and engages the protrusion 51B in the second space to restrain the tray 160 moved to the first location from moving further to the first isolator 110 side (−X). In other words the rest 52B has a function of making the tray 160 come to a rest at the first location by abutting against the protrusion 51B. The rest 52B is detachably (freely detachable) mounted to the −X side end part of the first guide unit 156B so that the tray 160 can be provided on the moving path of the protrusion 51B when moving the tray 160 in the −X direction. The rest 52B includes a first piece 521 and a second piece 522. The first piece 521 is in a state substantially parallel to the YZ plane, and is detachably attached to the end part on the −X side of the first guide unit 156B with, for example, a screw 523. The second piece 522 is bended from the end on the −Z side of the first piece 521 toward the +X side so to be inserted in the second space.

The first guide unit 156A and the second guide unit 161A have a protrusion 51A (second protruding piece) and a rest 52A (second abutment) that exhibit a function as the second stopper. The protrusion 51A and the rest 52A restrain the tray 160 moved to the second location from moving further to the second isolator 130 side (+X).

The protrusion 51A is a protruding piece that protrudes from the sixth part of the second guide unit 161A toward the +Y direction in the first space. For example, the protrusion 51A is provided on the −X side with regard to approximately the center of the second guide unit 161A in the longitudinal direction (X direction) of the second guide unit 161A.

The rest 52A is an abutment that abuts and engages the protrusion 51A in the first space to restrain the tray 160 moved to the second location from moving further to the second isolator 130 side (+X). In other words the rest 52A has a function of making the tray 160 come to a rest at the second location by abutting the protrusion 51A. The rest 52A is detachably (freely detachable) mounted to the +X side end part of the first guide unit 156A so that the tray 160 can be provided on the moving path of the protrusion 51A when moving the tray 160 in the +X direction. Note that the configuration of the rest 52A is similar to that of the rest 52B and thus the description thereof is omitted.

<Mounting>

The tray 160 to which the second guide units 161A, 161B are fixed, is mounted to the bottom plate 155 to which the first guide units 156A, 156B are fixed by, for example, the first mounting procedure or the second mounting procedure.

First Mounting Procedure

The rest 52A is disengaged from the first guide unit 156A. The end parts on the −X side of the sixth part of the second guide units 161A, 161B are each inserted into the first and second spaces from the +X side end of the first guide units 156A, 156B. In other words the tray 160 is mounted to the bottom plate 155 by sliding from the second workspace B side (+X) toward the transport space C side (−X). Thereafter, the rest 52A is mounted to the first guide unit 156A.

Second Mounting Procedure

The rest 52B is disengaged from the first guide unit 156B. The end parts on the +X side of the sixth part of the second guide units 161A, 161B are each inserted into the first and second spaces from the −X side end of the first guide units 156A, 156B. In other words the tray 160 is mounted to the bottom plate 155 by sliding from the first workspace A side (−X) toward the transport space C side (+X). Thereafter, the rest 52B is mounted to the first guide unit 156B.

Movement

For example, when a force is applied to the grip 164a in a direction from +X to −X, the tray 160 moves to the first isolator 110 side. When the tray 160 moves to the first location, the protrusion 51B and the rest 52B abuts and engages with each other. With such circumstances, the tray 160 is restrained from moving further to the first isolator 110 side and comes to a standstill at the first location. And for example, when a force is applied to the grip 164b in a direction oriented from −X to +X, the tray 160 moves to the second isolator 130 side. When the tray 160 moves to the second location, the protrusion 51A and the rest 52A abuts and engages with each other. With such circumstances, the tray 160 is restrained from moving further to the second isolator 130 side and comes to a standstill at the second location.

[2. Effects Etc.]

The isolator system 100 according to the present disclosure includes a first isolator 110 forming the first workspace A that is hermetically sealed from the ambient environment, a second isolator 130 forming the second workspace B that is hermetically sealed from the ambient environment, and a pass box 150 being provided between the first isolator 110 and the second isolator 130 and forming a transport space C that can communicate the first workspace A and the second workspace B while maintaining airtightness. The pass box 150 has a plate-like tray 160 for placing thereon articles used for work and a moving mechanism (rails R1 and R2) which enables the tray 160 to move to both the first isolator 110 side and the second isolator 130 side, at the bottom plate 155 of the transport space C. The grip 164a (first end) on the first isolator 110 side is positioned in the first workspace A when the tray 160 is moved to the first isolator 110 side, and the grip 164b (second end) on the second isolator 130 side is positioned in the second workspace B when the tray 160 is moved to the second isolator 130 side.

Hereby, for example, articles placed on the tray 160 in the pass box 150 can be easily taken out regardless of whether the worker works at the first isolator 110 or the second isolator 130. Therefore, the operability of the isolator system 100 can be improved.

Further, in the isolator system 100 according to the present disclosure, the first isolator 110 has a first opening H1 formed to the second side face 117a on the pass box 150 side, and the second isolator 130 has a second opening H2 formed to the side face 137b on the pass box 150 side. The pass box 150 has formed a first delivery opening 153 hermetically connected to the first opening H1 on the right side face 117a of the first isolator 110 and a second delivery opening 154 hermetically connected to the second opening H2 on the side face 137b of the second isolator 130. The first delivery opening 153 has provided a first door D1 capable of sealing the first delivery opening 153, and the second delivery opening 154 has a second door D2 capable of sealing the second delivery opening 154. The first door D1 can open and close a side of the first workspace A and the second door D2 can open and close a side of the second workspace B.

Hereby, for example, the doors on the two sides are opened to and close the inside so that the mounting area of the tray 160 can be secured and also allows the tray 160 to be taken out easily into the first workspace A or the second workspace B. Therefore, the operability of the isolator system 100 can be improved. Although in the present embodiment, the first door D1 was provided to the first delivery opening 153, and the second door D2 was provided to the second delivery opening 154, a configuration in which the first door D1 is provided to the first opening H1 and the second door D2 is provided to the second opening H2 can be adopted. In other words, it will do as long as at least one of the doors provided on the two sides can open and close the inside.

Furthermore, the moving mechanism of the isolator system 100 according to the present disclosure is provided to the bottom plate 155 of the transport space C and includes a rail R1 (first engaging part) which guides the movement of the tray 160 and a rail R2 (second engaging part) which is provided on the back side of the mounting face of the tray 160 for having articles used in work mounted thereon, and is engaged to the rail R1.

Hereby, for example, the tray 160 is strengthened so that the tray 160 is movable while having an article stably placed on the mounting face of the tray 160. And thus the operability of the isolator system 100 can be improved.

Yet further still, the two rails R1 and R2 according to the isolator system 100 of the present disclosure are linear and in parallel to the moving direction of the tray 160.

Hereby, for example, the movement of the tray 160 is made smooth. And thus the operability of the isolator system 100 can be improved.

Even further still, the two ends (first end and the second end) of the tray 160 according to the isolator system 100 of the present disclosure has formed a grip 164 bended downward from the mounting face of the tray 160.

Hereby, for example, the worker can hold the grips 164a, 164b to pull out the tray 160 allowing the tray 160 to be pulled out easily. And thus the operability of the isolator system 100 can be improved.

Even further still, the rail R1 according to the isolator system 100 of the present disclosure includes a spacer 162 which is fixed to the back face of the mounting face of the tray 160, and a first guide unit 161 which is fixed to the spacer 162 and restrains the tray 160 from coming off of the rail R2. The length of the spacer 162 in the vertical direction (Z direction) is configured to be longer than the length of the grips 164a, 164b in the vertical direction (Z direction).

Hereby, the moving range of the tray 160 can be widened. And thus the operability of the isolator system 100 can be improved.

Even further still, the moving mechanism of the isolator system 100 according to the present disclosure has provided a protrusion 51B and a rest 52B as the first stopper and a protrusion 51A and a rest 51A as the second stopper which restrain the moving range of the tray 160.

Hereby, the tray 160 can be restrained from being excessively pulled out by the worker and dropping and the like of articles can be restrained. And thus the operability of the isolator system 100 can be improved.

Even further still, the first guide units 156A, 156B and the second guide units 161A, 161B are each two linear members parallel to the moving direction (X direction) of the tray 160. The protrusion 51B, the rest 52B, the protrusion 51A, and the rest 51A are respectively provided to the second guide unit 161B, the first guide unit 156B, the second guide unit 161A and the first guide unit 156A. The first guide units 156A, 156B and the second guide units 161A, 161B have the first and second stoppers provided in this way.

Hereby, for example, the first and second stoppers can be miniaturized. And thus, for example, the space of the transport space C can be widened.

Even further still, the protrusion 51B protrudes from a location to the side closer to the +X side end of the second guide unit 161B. The protrusion 51A protrudes from a location to the side closer to the −X side end of the second guide unit 161A. The rest 52B engages with the protrusion 51B at the −X side end of the first guide unit 156B when exercising the function as the first stopper. The rest 52A engages with the protrusion 51A at the +X side end of the second guide unit 156A when exercising the function as the second stopper.

Hereby, for example, the tray 160 can be made to come to a standstill at the first or the second locations. Thus for example, there can be provided a convenient isolator system 100 which makes the moving of the devices mounted on the tray 160 to the first workspace A and the second workspace B easy.

Even further still, the rests 52A, 52B are respectively detachably attached to the first guide units 156A, 156B. Therefore, the tray 160 can be relatively easily mounted to the bottom plate 155 according to, for example, the first or the second mounting procedure.

Even further still, the first guide units 156A, 156B are in elongated states extending along the moving direction (X direction) of the tray 160 and are arranged in the Y direction that intersects the X direction. The second guide units 161A, 161B are in elongated states extending along the X direction and engage with the first guide units 156A, 156B. Since the each of the guide units are, for example, arranged in the Y direction in twos, for example, the tray 160 can be moved while the tray 160 is maintained in a substantially parallel state.

Even further still, the third parts of the first guide units 156A, 156B are bended to form a first and a second space between the bottom plate 155. The sixth part of the second guide units 161A, 161B is inserted between the first and the second spaces to move the tray 160 in the X direction.

Therefore, the tray 160 can be certainly moved in the X direction while the movement of the tray 160 in the vertical direction (Z direction) is in a restrained state.

Even further still, the rest 52A is detachably attached to the +X side end of the first guide unit 156A. The rest 52B is detachably attached to the −X side end of the first guide unit 156B. Hereby, the rests 52A, 52B can be easily detached. Therefore, the tray 160 can be further easily mounted to the bottom plate 155 by, for example, the first or the second mounting procedure.

As hereinabove, a description of the embodiment 1 was given as an example of technology disclosed in the present application. However, the technology according to the present disclosure is not limited to such and changes, replacements, additions, omissions and the like appropriately made to the embodiment is also applicable. Further, each of the components explained in the above embodiment 1 may be combined to create a new embodiment.

Further, since the aforementioned embodiment is for exemplifying the technology according to the present disclosure, various changes, replacements, additions, omissions and the like can be made within the range of the claims and the equivalents thereof.

The present disclosure can be applied to an isolator system configured to have a worker's hand inserted in a box-like experimental atmosphere for work.

What is claimed is:

1. An isolator system comprising:
   a first isolator forming a first workspace being hermetically sealed from an ambient environment;
   a second isolator forming a second workspace being hermetically sealed from the ambient environment; and
   a pass box provided between the first isolator and the second isolator and forming a transport space enabled to communicate the first workspace and the second workspace while maintaining hermeticity,
   wherein the pass box includes:
      a tray on which an article used in work is mounted, the tray having a first end on the first isolator side and a second end on the second isolator side,
      a moving mechanism configured to enable movement of the tray toward directions to both sides of the first isolator and the second isolator,
      the first end of the tray is located in the first workspace when the tray is moved to the first isolator side,
      the second end of the tray is located in the second workspace when the tray is moved to the second isolator side, and
   the first end and the second end of the tray each has a grip bended downward from a mounting face of the tray,
   wherein the moving mechanism includes:
      a first engaging part provided to a bottom face of the transport space and guides a movement of the tray,
      a second engaging part provided to the tray and is engaged to the first engaging part, and
      a spacer fixed between a back face of the mounting face of the tray and the first engaging part,
   wherein a length of the spacer in a vertical direction is configured to be longer than a length of the grip in the vertical direction, and
   wherein the first engaging part and the second engaging part are each configured with two linear members that are parallel to a moving direction of the tray.

2. The isolator system according to claim 1, further comprising:
   a first door configured to open and close a first opening between the first isolator and the pass box; and
   a second door configured to open and close a second opening between the second isolator and the pass box,
   wherein the first door can open and close a side of the first workspace, and
   the second door can open and close a side of the second workspace.

3. The isolator system according to claim 1, wherein the moving mechanism further includes:
   a first stopper configured to restrain a movement of the tray when the tray is moved to the first isolator side, and
   a second stopper configured to restrain a movement of the tray when the tray is moved to the second isolator side.

4. The isolator system according to claim 3, wherein
the first engaging part and the second engaging part are each configured with two linear members that are parallel to the moving direction of the tray,
the first stopper is provided to one of the two linear members, and
the second stopper is provided to an other of the two linear members.

5. The isolator system according to claim 4, wherein the first and the second stoppers are configured with a protrusion partly protruding in one of the first and the second engaging parts, and a rest provided to an other of the first and the second engaging parts and configured to engage with the protrusion.

6. The isolator system according to claim 5, wherein the rest is detachably attached.

7. The isolator system according to claim 1, wherein
the first engaging part has an elongated shape extending along the moving direction of the tray and has a first rail and a second rail arranged in a direction intersecting the moving direction, and
the second engaging part has an elongated shape extending along the moving direction and has a third rail and a fourth rail that engages with the first rail and the second rail, respectively.

8. The isolator system according to claim 7, wherein
the first rail and the second rail has a first and a second bended piece that is bent in the direction intersecting the moving direction to form a space between the bottom face, and
the third rail and the fourth rail has a first and a second insert piece that are inserted in the space to move the tray along the moving direction.

9. The isolator system according to claim 8, wherein the moving mechanism further includes:
a first stopper configured to restrain the tray from moving further to the first isolator side when the tray is moved to a first location on the first isolator side, and
a second stopper configured to restrain the tray from moving further to the second isolator side when the tray is moved to a second location on the second isolator side.

10. The isolator system according to claim 9, wherein the first stopper includes:
a first protruding piece configured to protrude from the first insert piece, and
a first abutment provided to the third rail and configured to abut against the first protruding piece inside the space to restrain the tray from further moving to the first isolator side when the tray is moved to the first location, and
the second stopper includes:
a second protruding piece configured to protrude from the second insert piece, and a second abutment provided to the fourth rail and configured to abut against the second protruding piece inside the space to restrain the tray from further moving to the second isolator side when the tray is moved to the second location.

11. The isolator system according to claim 10, wherein
the first abutment is shaped to be detachably attached to an end on the first isolator side of the third rail, and
the second abutment is shaped to be detachably attached to an end on the second isolator side of the fourth rail.

* * * * *